United States Patent [19]

Ejima et al.

[11] Patent Number: 5,610,284

[45] Date of Patent: Mar. 11, 1997

[54] METHOD OF PURIFICATION OF HUMAN BCDF

[75] Inventors: Daisuke Ejima; Yutaka Sato; Mayumi Watanabe; Masayo Date; Yoshiyuki Takahara, all of Kawasaki, Japan

[73] Assignee: Ajinomoto Co., Inc., Tokyo, Japan

[21] Appl. No.: 275,663

[22] Filed: Jul. 15, 1994

Related U.S. Application Data

[63] Continuation of Ser. No. 154,390, Nov. 18, 1993, abandoned, which is a continuation of Ser. No. 938,229, filed as PCT/JP92/00204, Feb. 25, 1992, abandoned.

[30] Foreign Application Priority Data

Feb. 26, 1991 [JP] Japan ................. 3-115689
Feb. 17, 1992 [JP] Japan ................. 4-029525

[51] Int. Cl.$^6$ .................. C07K 1/14; C12N 15/19
[52] U.S. Cl. ............. 530/412; 530/416; 530/417; 530/422; 530/425; 530/351; 530/426; 435/69.52; 435/71.1
[58] Field of Search ............. 435/69.1, 69.52, 435/240.2; 514/2, 12; 530/351, 412, 416–417, 422, 425, 426, 395

[56] References Cited

U.S. PATENT DOCUMENTS

| | | |
|---|---|---|
| 4,511,503 | 4/1985 | Olson et al. ............. 260/112 |
| 5,008,377 | 4/1991 | Patroni et al. . |
| 5,043,430 | 8/1991 | Yoshikawa . |
| 5,051,497 | 9/1991 | Fanning et al. . |

FOREIGN PATENT DOCUMENTS

| | | |
|---|---|---|
| 0254399 | 1/1988 | European Pat. Off. . |
| 257406 | 3/1988 | European Pat. Off. . |
| 0257406 | 3/1988 | European Pat. Off. . |
| 61-257931 | 11/1986 | Japan . |
| 2-186996 | 7/1990 | Japan . |
| 2138004 | 10/1984 | United Kingdom . |

OTHER PUBLICATIONS

Marston (1986) Biochem J. vol. 240 pp. 1–12.
Annals of the New York Academy of Sciences, vol. 557, Jun. 15, 1989, pp. 192–199, Lucien A. Aarden, "Hybridoma Growth Factor".
Biotechnology, vol. 6, No. 7, Jul. 1988, pp. 806–809, Yoshihiro Asagoe, et al., "Human B-Cell Stimulatory Factor-2 Expressed in *Escherichia coli*".
Biotechnology, vol. 8, Nov. 1990, pp. 1036–1040, Hisashi Yasueda, et al., "High-Level Direct Expression of Semi-Synthetic Human Interleukin-6 in *Escherichia coli* and Production of N-Terminus Met-Free Product".
Eur. J. Biochem., vol. 198, No. 3, Jun. 1991, pp. 541–547, Rosaria Arcone, et al., "Single-Step Purification and Structural Characterization of Human Interleukin-6 Produced in *Escherichia coli* from a T7 RNA Polymerase Expression Vector".
Proceedings of the National Academy of Sciences, vol. 85, Dec. 1988, pp. 9738–9742, Clay B. Siegall, et al., "Cytotoxic Activity of an Interleukin 6-Pseudomonas Exotoxin Fusion Protein on Human Myeloma Cells".

*Primary Examiner*—John Ulm
*Assistant Examiner*—Prema Mertz
*Attorney, Agent, or Firm*—Oblon, Spivak, McClelland, Maier & Neustadt, P.C.

[57] ABSTRACT

There are disclosed (i) a purification process for obtaining a human BCDF having the intramolecular disulfide linkage and the stereostructure of natural type human BCDF which comprises subjecting to an oxidation reaction and a refolding treatment a reduced type human BCDF obtained by culturing a microorganism having a human BCDF gene integrated therein and solubilized with guanidine hydrochloride, characterized in that after the oxidation reaction, a gel filtration chromatographic treatment is conducted under the conditions of the guanidine hydrochloride concentration adjusted to 4–7M; (ii) a purification process for obtaining a natural type human BCDF monomer by removing the organic solvent from an organic solvent-containing solution of human BCDF, characterized in that the solution is passed through a gel filtration chromatographic column equilibrated with an organic solvent, followed by eluting according to a stepwise or linear gradient program; and (iii) a human BCDF purification process comprising an ion exchange chromatographic treatment and a reversed phase HPLC step, in combination (i) or (ii). According to these purification processes, it becomes possible to remove the impurities derived from a microorganism and human BCDF analogs, and the thus obtained natural type human BCDF has a high purity and can be utilized for pharmaceutical preparations.

18 Claims, 6 Drawing Sheets

METHOD OF PURIFICATION OF HUMAN BCDF

This application is a continuation of application Ser. No. 08/154,390, filed Nov. 18, 1993, abandoned, which is a continuation of Ser. No. 07/938,229, filed Oct. 26, 1992, abandoned, which was filed as International Application No. PCT/JP92/00204 on Feb. 25, 1992.

TECHNICAL FIELD

The present invention relates to a purification method of human B-cell differentiation factor (hereinafter referred to as human BCDF), which is useful for pharmaceutical preparations. More particularly, the invention relates to a method of separating pure human BCDF usable as medicines and guaranteed in its purity and safety, from cultured broths of a microorganism having human BCDF-DNA integrated therein, or a human BCDF-DNA integrated microorganism.

BACKGROUND ART

Human BCDF, which is a factor that differentiates human B cells into antibody-producing cells, had its cDNA cloned in 1986 (Nature, 324, 73 (1986)). Later, this substance has come to be called B-cell stimulatory factor-2 (BSF-2) or interleukin 6 (IL-6), and its properties have been clarified on the whole (molecular weight: about 21,000; isoelectric point: about 6.2). It has been also reported that human BCDF showed various bioactivities. Among those activities, there are included medicinal activities such as stem blood cell proliferating action, the action to differentiate their precursor cells into platelets, and the action to differentiate B lymphocytes into antibody-producing cells. Thus, utilization of human BCDF is expected in the field of medicine, as, e.g., a medicinal preparation for making up for the decrease of hemocytes resulting from the use of a carcinostatic agent or bone marrow transplantation, or a medicinal preparation for reinforcing the vaccine action.

The present inventors have already disclosed some methods of simply and effectively separating pure human BCDF from human BCDF cultured broths obtained by using, as production host, an *Escherichia coli* having cDNA for human BCDF integrated therein (see Japanese Patent Applications Kokai Nos. Hei 1-83094, Hei 1-300898 and Hei 2-186996). These methods, however, are not always satisfactory for removing impurities such as analogs of human BCDF, said impurities having been recognized in the course of study of the techniques for separating pure human BCDF from human BCDF cultured broths. Also, the degree of purification achievable by these methods, although satisfactory for laboratory research, is still unacceptable for the production of human BCDF to be used for medicine. For human BCDF to be used as medicine, it is necessary to establish a practical purification process on the premise that a medicinal base free of any substance harmful to the human body is industrially produced at a small cost and with a high purity sufficient for safe administration to man.

It is generally known that when a physiologically active protein is produced by using a recombinant DNA in *E. coli* as host, there may occur contamination with an analog protein partially differing in primary structure from the natural type or an analog protein differing in disulfide linkage from the natural type. Also, as is known in connection with interleukin 2 and interferon, there may be cases where a desired protein is contaminated with a high-molecular weight substance formed as a result of inter molecular association by non-covalent bond, said desired protein being normally supposed to exist as a monomer. Further, there are cases where an analog is produced as a result of cleavage or partial modification of a desired protein or variation of a desired protein in primary structure or stereo-structure in the process of purification. These analogs involve the danger of causing a harmful immunoreaction by producing an unnecessary antibody when they are administered repeatedly to the human body. The existence of inter molecular aggregates of human BCDF was discovered for the first time by the present inventors, as described below, and therefore its separation method has not been known.

Further, there has not been disclosed a combination of the purification techniques according to which
(1) formation of denatured proteins from human BCDF may be minimized, which denatured proteins may cause lowering of the physiological activities of human BCDF, and
(2) proteins derived from the microorganism which may be harmful to the human body may be removed,
(3) whereby a highly pure human BCDF cleared of exothermic substances (such as endotoxin) derived from the microorganism or included in the course of the purification process, along with the above-mentioned techniques for removing the analogs.

Lymphokines such as human BCDF normally works in vivo at a concentration of as little as about several pg/ml, but for the purpose of treating a lymphokine as a medicinal base, it is desirable to treat it at a high concentration of as much as about several mg/ml. The reasons are that 1) since high dosage toxicity tests can be conducted, safety evaluation of the lymphokine can be made with higher accuracy, 2) when a medicinal preparation is made from a base, it can be easily adjusted to an appropriate concentration for administration even if various adjuvants are added, which, in turn, means that it is easy to make a medicinal preparation, and 3) since the purification process can be carried out on a small scale, it becomes possible to simplify the operation and apparatus concerned. Lymphokines are, however, generally highly hydrophobic, and the risk of inter molecular association, precipitation or denaturation increases as the concentration increases, so that in the purification of human BCDF according to the present invention, it was necessary to elaborate the purification conditions, different from the purification under the low concentration conditions for cultures of cells, etc.

DISCLOSURE OF THE INVENTION

The object of the present invention is to provide a purification method which enables efficient production on an industrial scale of a highly pure, stable and highly concentrated human BCDF solution which is free of impurity proteins or endotoxins derived from the production host, contaminants generated in the purification process and human BCDF analogs such as variants differing in primary structure or aggregates (highmolecular weight substances) derived from the human BCDF.

As a result of assiduous studies for achieving the object, the present inventors have found, in order to purify human BCDF in the bacterial cells obtained by mass culture of an *E. coli* having a human BCDF gene integrated therein, an industrially appliable purification process for purifying human BCDF to such a high purification degree as allowing human administration, in which process the most use is made of (1) steps for solubilization (extraction) using a highly concentrated protein denaturing agent, and oxidation reaction and refolding, (2) steps for removing bacterial cell proteins, endotoxins, primary structure variants of human BCDF, etc., by using the ion exchange chromatography and the reversed phase high performance liquid chromatography (hereinafter, referred to as reversed phase HPLC) and (3) steps for removing protein denaturing agent, organic solvents and molecular aggregates of human BCDF by using the gel filtration method. The present invention has been made on the basis of such findings.

Thus, the present invention relates to (1) a human BCDF purification process comprising subjecting to an oxidation reaction and a refolding treatment a reduced type solubilized human BCDF solution formed by solubilizing human BCDF in a human BCDF cultured broth obtained by culturing a microorganism having a human BCDF gene integrated therein, characterized in that after the reduced type solubilized human BCDF solution has been subjected to the oxidation reaction, the resultant oxidized type human BCDF solution, after adjusted to 4–7M in its guanidine hydrochloride concentration, is subjected to the gel filtration chromatography; and (2) a human BCDF purification process comprising removing the organic solvent from a human BCDF solution containing an organic solvent by passing a developing solvent through a gel filtration chromatographic column, characterized by the steps of (i) passing a developing solvent containing the organic solvent through the gel filtration chromatographic column, (ii) then feeding the human BCDF solution to the column, and (iii) passing the developing solvent through the column with the amount of the organic solvent in the developing solvent being less than that in the developing solvent used in (i) above and decreased according to a stepwise gradient or linear gradient program, whereby an aqueous human BCDF solution free of the organic solvent is obtained.

The invention relates further to (3) a process for separating a highly pure human BCDF from a human BCDF cultured broth obtained by culturing a microorganism having a human BCDF gene integrated therein, comprising the steps of:

(i) subjecting to an oxidation reaction a reduced type solubilized human BCDF solution formed by solubilizing human BCDF in a human BCDF cultured broth, and then subjecting to the gel filtration chromatography the resultant oxidized type human BCDF solution after adjusted to 4.0–7.0M in its guanidine hydrochloride concentration, (ii) conducting an ion exchange chromatographic treatment comprising feeding the human BCDF solution to a chromatographic column packed with a gel support having as ligand an ion exchanger whose base is a polysaccharide, dextran or a synthetic polymer, and then the elution being carried out with an eluent being changed in its salt concentration, to thereby purify the human BCDF, (iii) conducting a reversed phase chromatographic treatment by passing the human BCDF solution through a column packed with a reversed phase chromatographic support having as ligand an alkyl group of 1–8 carbon atoms and with a pore size of 250 Å or more, to thereby purify the human BCDF, and (iv) carrying out a gel filtration chromatographic treatment by first passing a developing solvent containing an organic solvent through a gel filtration chromatographic column, then feeding the human BCDF solution to the column, and passing the developing solvent through the column with the amount of the organic solvent in the developing solvent being less than that in the first used developing solvent and decreased according to a stepwise gradient or linear gradient program, whereby an aqueous human BCDF solution cleared of the organic solvent is obtained.

The present invention is described in detail below.

The starting material to be purified in accordance with the present invention is a human BCDF cultured broth obtained by culturing a microorganism having a human BCDF gene integrated therein, for example, a human BCDF gene integrated *E. coli*. Usually, human BCDF in a human BCDF cultured broth mostly exists as insoluble granules within the microorganism cell, and such human BCDF granules may be used as the starting material. Most of such human BCDF exists in the reduced type in which the four component cysteines ($^{44, 50, 73, 83}$Cys) have a free thiol structure, forming no disulfide linkage.

Now, the step for solubilizing human BCDF in the form of insoluble granules is described. According to a conventional method, human BCDF insoluble granules, after suspended in distilled water if necessary, are centrifuged at a relatively low rotating speed to wash away the adhering impurities. The resultant pellets are suspended in a low-concentration (1–10 mM) EDTA solution, and then the reduced type human BCDF is solubilized with a high-concentration (e.g., 6M) solution of guanidine hydrochloride as a protein denaturing agent, so as to give a human BCDF solution having a final human BCDF concentration of 1.0–3.0 mg/ml. If necessary, urea or the like may be added as protein denaturing agent. The suspension is stirred slowly at 10°–35° C. preferably 20°–28° C. for 1–4 hours, while keeping the pH at or below 5.5–6.0, whereby inter molecular aggregation by formation of intermolecular disulfide linkage. Usually, natural type human BCDF has four cysteines ($^{44, 50, 73, 83}$Cys) in its molecule, and the four form two intramolecular disulfide linkages ($^{44}$Cys-$^{50}$Cys and $^{73}$Cys-$^{83}$Cys). Since most of the cysteines are of a free thiol structure in solubilized human BCDF as mentioned before, it is necessary to carry out an oxidation reaction and a refolding treatment described below.

The step of oxidation reaction and refolding treatment will described below, by setting out first their characteristic features.

As stated above, natural type human BCDF has intramolecular disulfide linkages, while human BCDF generated and accumulated within cells of a microorganism such as *E. coli* is in the reduced state (thiol type) and in the form of insoluble aggregates (inclusion body). Therefore, to convert this into natural type human BCDF, formation of intramolecular disulfide linkages and the natural type stereostructure (original higher-order structure prior to denaturing) is required. The method of oxidation reaction and refolding treatment according to this invention is characterized by that human BCDF is first subjected in the completely denatured state, the human BCDF being in the reduced state, to an oxidation reaction in a high-concentration guanidine hydrochloride solution to perfectly form intramolecular disulfide linkages in monomer molecules of the human BCDF, whereby oxidized type human BCDF is formed, and that salts such as guanidine hydrochloride are then removed while maintaining a specified guanidine hydrochloride concentration, whereby the stereostructure of natural type human BCDF results. This treating step according to the present invention is advantageous over a conventional oxidation reaction and refolding treatment, in that the time required for the step is shorter, that the yield of human BCDF can be prevented from lowering due to precipitation in the course of the reaction, and that the increase in liquid amount due to dilution, etc., can be minimized or eliminated.

The oxidation reaction step is described in detail below. A solubilized human BCDF solution may be diluted with a guanidine hydrochloride solution, if necessary, but it is suggested to adjust the guanidine hydrochloride concentration to 4–7M, preferably 5.0–6.0M. When the guanidine hydrochloride concentration is less than 4M, the human BCDF is recovered in lower yields, which is of course not preferable. The concentration of human BCDF is not specifically limited as far as human BCDF is dissolved, and may be selected from within a range of to 0.1–2.0 mg/ml, preferably 0.5–0.8 mg/ml. As for the pH condition, in order to allow dissociation of the thiol groups, it is recommended to add a basic substance, for example, an aqueous solution of sodium hydroxide, to adjust the pH to 6.5–9.0, preferably 8.0–8.6. Under these conditions, the oxidation reaction of human BCDF is carried out with slow stirring at a temperature of 10°–35° C., preferably 20°–28° C., for a period of 3–24 hours, preferably 10–15 hours, whereby complete formation of natural type intramolecular disulfide linkages is effected to give oxidized type human BCDF. From the studies using $^{13}$C-NMR, it is noted in connection with partially reduced type human BCDF (for example, the one in which $^{73}$Cys and $^{83}$Cys are linked but $^{44}$Cys and $^{50}$Cys remain unlinked), intramolecular disulfide linkage (oxidation) is formed in a very short time when the pH is 6.5 or above, while there slowly takes place intramolecular disulfide linkage formation, although the human BCDF is relatively stable, when the pH is not more than 5 whereby natural type intramolecular disulfide linkage (oxidized type human BCDF) is formed.

Further, to complete formation of natural type disulfide linkage in a shorter period of time, it is suggested to add reduced type and oxidized type glutathiones in an appropriate combination (each in a concentration of 0.002–0.5 mM). Addition of too much an amount of glutathione (specifically, when its concentration is 1 mM or more in the case of reduced type glutathione and 0.1 mM or more in the case of oxidized type glutathione.) is undesirable because there may be formed a hybrid disulfide in which human BCDF and glutathione are directly bonded by disulfide linkage. The progress in formation of intramolecular disulfide linkage in human BCDF can be confirmed from the variation in retention time of a chromatogram by the reversed phase HPLC (using, for example, "214TP54" ex Vydac). The thus obtained preliminarily purified BCDF solution is stable for at least one week under a low temperature condition of 3°–10° C.

Next, there is required a step in which the human BCDF is subjected to refolding while removing mainly guanidine hydrochloride used in the previous step. As this step, a liquid chromatographic treatment, especially a gel filtration chromatographic treatment is effective. As the chromatographic support, there can be used polysaccharides, dextran, their chemically modified versions or synthetic polymers with a fractional molecular weight of 5,000 or less. Typical examples of supports include "Sephadex G-25" (ex Pharmacia Inc.), "Cellulofine GH-25" (ex Chisso Co., Ltd.), "Toyopearl HW-40" (ex Tosoh Co., Ltd.) and "Cellulose CW-35" (ex Tosoh Co., Ltd.), but are not limited thereto. A chromatographic support is packed in a column and is equilibrated with a buffer solution. As the buffer solution for equilibration, there can be used a 5–50 mM acetic acid or formic acid buffer solution (pH 4.0–5.8) in consideration of the next step, and as the counter cations, there can be used sodium ions, potassium ions, ammonium ions and the like. Such a support equilibrated with such a buffer solution is loaded with the human BCDF solution obtained in the previous step in an amount of 0.15–0.24 ml per 1 ml of the support, and developing and eluting is carried out with the use of such a buffer solution, whereby a human BCDF fraction is obtained. In this operation, if contaminants (proteins, glycoprotein, glycolipid, etc., derived from bacterial cells) in a human BCDF solution are also to be removed to obtain a higher purifying effect, an appropriate chromatographic support should be selected and the concentration or pH of such an equilibrating buffer solution should be properly controlled. For example, when "Sephadex G-25" is used as the chromatographic support and a 5–15 mM, preferably 8–10 mM sodium acetate buffer solution having a pH of 4.7–5.3, preferably 4.9–5.1 is used as the equilibrating buffer solution, the contaminants show a relatively strong affinity for the support, and as a result, the human BCDF fraction can be better separated from the guanidine hydrochloride and the contaminants.

A human BCDF thus obtained according to such a gel filtration chromatographic step has the intramolecular disulfide linkage and stereostructure of natural type BCDF, and its protein purity, as determined from the reversed phase HPLC for analysis and SDS-PAGE, is higher than 80%, usually higher than 90%. Also, the human BCDF fraction is a clean solution substantially free of precipitates, and can remain stable under an aseptic condition at a low temperature of 3°–10° C. for at least 10 days. The progress in the reaction in the step of the oxidation reaction and the refolding treatment can be confirmed by measuring $^{13}$C-NMR of human BCDF in which carbonyl carbons of an amino acid such as cysteine or phenylalanine have been selectively labelled with $^{13}$C.

To prepare a human BCDF of medicinal grade from a thus obtained human BCDF solution, it is essential to conduct a further purification by the ion exchange chromatography and the reversed phase HPLC, whereby the still remaining contaminants, especially proteins derived from the microbial cells, endotoxin and primary structure variants of human BCDF can be eliminated. The term "primary structure variants" of human BCDF used here refers to human BCDF in respect of which the peptide linkages are partly severed or the component amino acids are partly oxidized, and it is supposed that such a human BCDF is usually formed in the course of cultivation and/or at the stage of solubilization.

By carrying out a purification treatment by the ion exchange chromatography, especially, it is possible to remove substantially all of the contaminants and endotoxin contained in human BCDF. The ion exchanger to be used here may be either a cation exchange chromatographic support or an anion exchange chromatographic support.

As such a cation exchange chromatographic support, there can be employed any gel having as ligand a weakly acidic or strongly acidic cation exchanger whose base is a polysaccharide, dextran, a synthethic polymer or the like. Typical examples of such support include "CM Sepharose FF" (ex Pharmacia Inc.) and "CM Cellulofine C-500" (ex Chisso Co., Ltd.). A support is packed in a column, equilibrated with an acetic acid or formic acid buffer solution (pH 4.5–5.5), and then loaded with a human BCDF solution (Protein being in an amount of 1–10 mg per 1 ml of support), whereby the human BCDF is adsorbed, followed by through washing with the equilibrating buffer solution. Then, the adsorbed human BCDF is eluted, using the equilibrating buffer solution while being added concentration-gradientwise with a salt such as sodium, potassium or ammonium chloride, or a sodium, potassium or ammonium salt of acetic acid or formic acid. For example, elution is carried out by using a 10 mM sodium acetate equilibrating buffer solution (pH 5.0) and a 0.5M sodium acetate buffer solution (pH 5.0) and a 0.5M sodium acetate buffer solution (pH 5.5), while the ratio of the latter is being raised gradually (linear gradient elution). Such an eluent can be used in a total amount of about 10 times the column capacity. The pH of a acetic acid of formic acid buffer solution to be used as eluent may be higher by 0.5–1.0 than that of an equilibrating buffer solution. A thus obtained human BCDF is a natural type human BCDF. The protein purity of this fraction is at least 95%, usually higher than 98%, and the endotoxin content is not more than 0.5 endotoxin unit (EU) per 1 mg of protein.

On the other hand, as such an anion exchange chromatographic support, there can be used any gel having as ligand a weakly basic or strongly basic anion exchanger whose base is a polysaccharide, dextran, a synthetic polymer or the like. Examples of such support include "DEAE Sepharose FF" (ex Pharmacia Inc.) and "DEAE Cellulofine A-500 (ex Chisso Co., Ltd.). A support is packed in a column, equilibrated with a buffer solution having a buffer action at a pH of 7.5–10.0 (such as tris-diethanolamine), then loaded with a human BCDF solution (in an amount of 1–10 mg of protein per 1 ml of carrier), and sufficiently washed with an equilibrating buffer solution.

A human BCDF solution to be treated in this way is preferably a one prepared by adding the equilibrating buffer solution to a human BCDF solution containing no denaturing agent to adjust its pH to 8.5–9.5.

Thereafter, the human BCDF is eluted with an equilibrating buffer solution while being added gradient-wise a salt, for example, a chloride such as sodium chloride or potassium chloride. For example, elution is carried out by using a 50 mM tris-hydrochloride equilibrating buffer solution (pH 8.5) and an aqueous 0.5 mM sodium chloride solution, while the ratio of the latter is being increased gradually (linear gradient elution). Such an eluent can be used in a total amount of about 10 times the column capacity. A thus obtained human BCDF is of course a natural type human BCDF. The protein purity of this fraction is at least 90%, and the endotoxin content is not more than 50 EU per 1 mg of protein.

A human BCDF solution thus obtained by said cation or anion exchange chromatographic treatment, when kept aseptically at a low temperature of 3°–10° C., can remain stable for at least one month.

Next, the reversed phase HPLC treatment is suited for the removal of the remaining contaminants, endotoxin and primary structure variants of human BCDF. As a support for the reversed phase HPLC, there can be used one which has as ligand an alkyl group of 1–8 carbon atoms or the like and whose base is silica gel or a synthetic polymer with a pore size of 250 Å or more. Examples of such support are "214 TP 1022" (ex Vydac) and "YMC AP-803" (ex Yamamura Kagaku Kenkyusho, Ltd.). Other supports can be used as well.

As the eluting agent is recommended a combination of an aqueous 0.01–1.0% solution of trifluoroacetic acid, heptafluorobutyric acid, acetic acid, or formic acid and a sodium salt thereof, as an ion pair reagent, and having its pH adjusted to 2.0–5.5 and an organic solvent such as acetonitrile, ethanol, propanol or the like containing 0.01–1.0% of such an ion pair reagent. It is also desirable that a human BCDF solution to be treated by the reversed phase HPLC be properly added with distilled water, etc., to lower the salt concentration in the solution enough to make the final salt concentration less than 100 mM, and adjusted in its pH to 2.0–5.5, preferably 3.0–3.5 by adding such an ion pair reagent. After loading the chromatographic support with the human BCDF solution in an amount of 1–4 mg of protein per 1 ml of chromatographic support, a purrer human BCDF is separated by eluting with an eluting agent in respect of which the organic solvent concentration is raised gradually by changing the eluting agent gradient-wise. Since the separation efficiency of human BCDF from impurities such as contaminants, endotoxin and primary structure variants is greatly affected, especially by the ion pair reagent concentration and the pH, it is advisable to select the optimal conditions in conformity to the content of these impurities.

A human BCDF obtained in combination with the ion exchange chromatographic treatment has a protein purity of at least 99% (No contaminants are detected by the SDS-PAGE analysis) and an endotoxin content of not more than 0.1 EU per 1 mg of protein. Also, a thus obtained human BCDF, when kept aseptically at a low temperature of 3°–10° C., remains stable for at least one week.

Since a human BCDF fraction obtained in the reversed phase HPLC step contains some organic solvent, there is required a step for removing the organic solvent. The present inventors have, however, found that when the organic solvent is simply to be removed, inter molecular association of human BCDF can proceed to the formation of human BCDF aggregates, which means, in turn, a sizable reduction in recovery yield of the human BCDF monomer. It has been revealed by the GPC-LALLS method (A. C. Ouano; Journal of Polymer Science, 12, 1151–1162, 1974) that such a human BCDF aggregate is principally in the dimeric form, and it is supposed that the monomeric molecules and associated in an aggregate molecule by non-convalent bond principally based on a hydrophobic interaction.

Since human BCDF in a human BCDF fraction obtained in the reserved phase HPLC step undergoes a reversible change between association and dissociation with addition of an appropriate amount of an organic solvent, a specific technique is required for removing the organic solvent. As organic solvent removing methods, there are usually conceivable the gel filtration chromatography, membrane dialysis, ultrafiltration, concentration under reduced pressure, freeze-drying, and phase separation by cooling (See Japanese Patent Application Kokai No. Hei 1-83094). However, concentration under reduced pressure and freeze-drying can not be applied because according to these methods such human BCDF aggregates are formed in an amount of as much as 60–80%.

According to the present invention, the gel filtration chromatography is employed as the desirable organic solvent removing method, and can be used, if necessary, in combination with one or more methods as mentioned above. A gel filtration chromatographic support to be used in this step can be the same as the chromatographic support used in the refolding treatment step as explained above. Such a support is packed in a column, and loaded with a human BCDF solution containing an organic solvent. A developing solvent containing an organic solvent is passed through the column with the amount of the organic solvent contained in the developing solvent being decreased either stepwise or linearly, whereby a human BCDF solution free of the organic solvent initially contained. Thus, according to the present invention, it is possible to minimize formation of human BCDF aggregates by gradually removing the organic solvent from a human BCDF solution containing an organic solvent.

The method will be specifically described below.

A column-packed gel filtration chromatographic support is equilibrated with a 5–50 mM buffer solution of an organic acid such as acetic acid or a salt thereof containing 5–50% preferably 7–15% of an organic solvent such as acetonitrile, ethanol or propanol, then loaded with a human BCDF solution containing an organic solvent in an amount of 0.15–0.24 ml per 1 ml of the support. Elution is carried out by passing through the column such a buffer solution as the developing solvent to collect a human BCDF fraction. Subsequently, a column-packed gel filtration chromatographic support similar to that described above is equilibrated with a 3–20 mM buffer solution of an alkaline metal salt of an organic acid such as acetic acid, formic acid or citric acid, having a pH of 3.5–7.5, preferably 4.0–5.5, and containing no organic solvent, and then loaded with the human BCDF fraction obtained in the previous gel filtration chromatographic treatment in an amount of 0.15–0.34 ml per 1 ml of the support. Developing is carried out with such a buffer solution.

A human BCDF fraction obtained by such a two-stage gel filtration chromatographic treatment according to a stepwise program has the same level of protein purity as a human BCDF fraction obtained in the reversed phase HPLC step, and a content of human BCDF aggregates of not more than 10%, usually not more than 5%. This human BCDF fraction, when kept aseptically at a low temperature of 3°–10° C., remains stable for at least one week.

However, according to a gel filtration chromatographic treatment in which a gel filtration chromatographic support is directly equilibrated with a developing solvent (buffer solution)containing no organic solvent, a human BCDF solution containing an organic solvent is then fed, and such a developing solvent alone is finally passed through the column, there takes place association of more than 40% of the human BCDF irrespective of the pH of the developing solvent and the kind of the organic acid salt used. This treatment is, therefore, unsuited for the object of this invention. Even if, however, a human BCDF solution is subjected to a one-stage gel filtration chromatographic treatment, formation of human BCDF aggregates can be effectively prevented by equilibrating the gel filtration chromatographic support with a buffer solution of an organic acid or a salt thereof containing an organic solvent such as acetonitrile, ethanol or propanol as described above, followed by decreasing the amount of the organic solvent in such a developing solvent according to stepwise gradient or linear gradient program.

If it is desired to further concentrate human BCDF and/or to remove a small amount of a decomposition product of human BCDF formed during storage of a human BCDF solution cleared of the organic solvent by gel filtration, a cation exchange chromatographic treatment is, if necessary, recommended. That is, a gel having as ligand a weakly acidic or strongly acidic cation exchange whose base is a polysaccharide, dextran or a synthetic polymer, such as "CM Sepharose FF" (ex Pharmacia Inc.) or "CM Cellulofine C-500" (ex Chisso Corp.), is packed in a column, equilibrated with a 15–20 mM buffer solution (pH 4.0–5.5) of a sodium or potassium salt of acetic acid, formic acid or citric acid, and loaded with a human BCDF fraction obtained in the preceding step in an amount of 10–30 mg protein per 1 ml of the chromatographic support. Then, the non-adsorbed portion is throughly washed out with an equilibrating buffer solution. Thereafter, the human BCDF is preferably subjected to a gradient elution by adding a salt such as sodium chloride to the equilibrating buffer solution in a successive way up to a concentration of 10–500 mM, or the human BCDF is preferably eluted with a 5–20 mM, preferably 8–15 mM sodium citrate buffer solution with a pH of 6.0–6.7, preferably 6.4–6.6, and added with a salt such as sodium chloride up to 30–100mM, preferably 40–60 mM, instead of the former eluent. Especially the latter elution method is effective for obtaining a highly concentrated human BCDF solution without increasing aggregates of human BCDF. Human BCDF has a sequence ($^{140}$Asp-$^{141}$Pro) which thends to be severed under an acidic condition, and if such severance has occurred during storage, the severance product can be removed by this method of treatment. The purity of a thus obtained human BCDF is increased since the content of such severance product is decreased, and the concentration is drastically elevated to a level of 3–8 mg/ml.

Incidentally, in a human BCDF solution which has been subjected to an organic solvent removing treatment or in a human BCDF solution resulting from concentrating that solution by a cation exchange chromatographic treatment, there may remain a slight amount of human BCDF aggregates. In such a case, such aggregates may be removed by separation by subjecting such a solution to a gel filtration chromatographic treatment. For such a treatment, there is used a gel filtration support whose base is dextran, dextran-crosslinked agarose, hydrophilic silica gel or a synthetic polymer, such as "Sephacryl S-200" and "Superdex 75" (both ex Pharmacia Inc.), and "TSK G-2000SW" (ex Tosoh Co., Ltd.). Such a support is equilibrated with a 5–100 mM, preferably 10–20 mM buffer solution of a sodium or potassium salt of citric acid, phosphoric acid or a mixture thereof with the pH adjusted to 5–8, preferably 6.0–7.0, and then loaded with a human BCDF solution obtained by an organic solvent removing treatment of a subsequent cation exchange chromatographic treatment in an amount of 0.01–0.05 ml per 1 ml of support. The chromatogram is developed with such an equilibrating buffer solution, whereby there can be obtained a pure human BCDF monomer separated from human BCDF aggregates. Incidentally, human BCDF is high in hydrophobicity and often has an affinity for a gel filtration chromatographic support, and therefore, when a salt such as sodium chloride is added for the purpose of adjusting the osmotic pressure, such addition is preferably made after the above-said step.

With respect to a human BCDF solution (0.1–5 mg/ml concentration) obtained by combining (i) the step of oxidation reaction of a solubilized human BCDF solution and refolding treatment, (ii) the step of an ion exchange chromatographic treatment and a reversed phase HPLC treatment, and (iii) the step of removing the organic solvent by the gel filtration chromatography for separating a pure human BCDF from a human BCDF cultured broth obtained by culturing a microorganism having a human BCDF gene integrated therein, there is detected no band attributable to the contaminants in SDS-PAGE using the silver dyeing method, a single peak appears in the reversed phase HPLC, the ion exchange HPLC and the gel filtration HPLC, and the human BCDF is identified as natural type human BCDF by $^{13}$C-NMR, etc. Also, the concentration of the protein derived from the microorganism in such a human BCDF solution is not more than several ppm, when measured by the Western blotting using a polyclonal anti-*Escherichia coli* protein antibody prepared in the usual way employing as antigen protein derived from a microorganism (e.g., *E. coli*) or its partly purified version, and by an enzyme immunoassay (ELISA) using such an antibody. Further, the endotoxin content is not more than 0.1 EU (usually not more than 0.01EU) per 1 mg of human BCDF. The above-described high quality indicates that a human BCDF obtained according to the purification method of this invention is usable as an ingredient for pharmaceutical preparations to be used for the therapeutical purposes. The human BCDF solution obtained by the method of this invention can be worked into a stable pharmaceutical preparation by immediately subject-

BEST MODE FOR CARRYING OUT THE INVENTION

The present invention will be described concretely below with reference to the examples thereof.

EXAMPLE 1

*Eschericia coli* HB 101/pBSF2-SD7 AJ 12448 (FERM P-10758, FERM BP-3753) having a human BCDF coding DNA integrated therein was cultured in a synthetic medium, while human BCDF was accumulated voluminously as insoluble granules in the bacterial cells by the tryptophan promoter being induced with indoleavetic acid (IAA) (according to the method described in Japanese Patent Application Kokai No. Hei 3-53884).

A suspension of the granules (10 mM EDTA, 1.6 L) was prepared according to an ordinary method (i.e., the method described in Japanese Patent Application Kokai No. Sho 61-257931). The suspension was added with guanidine hydrochloride in such an amount that its final concentration became 6M, and stirred at room temperature and a pH of about 5.5 for 4 hours, whereby the human BCDF was solubilized.

Figure 1:
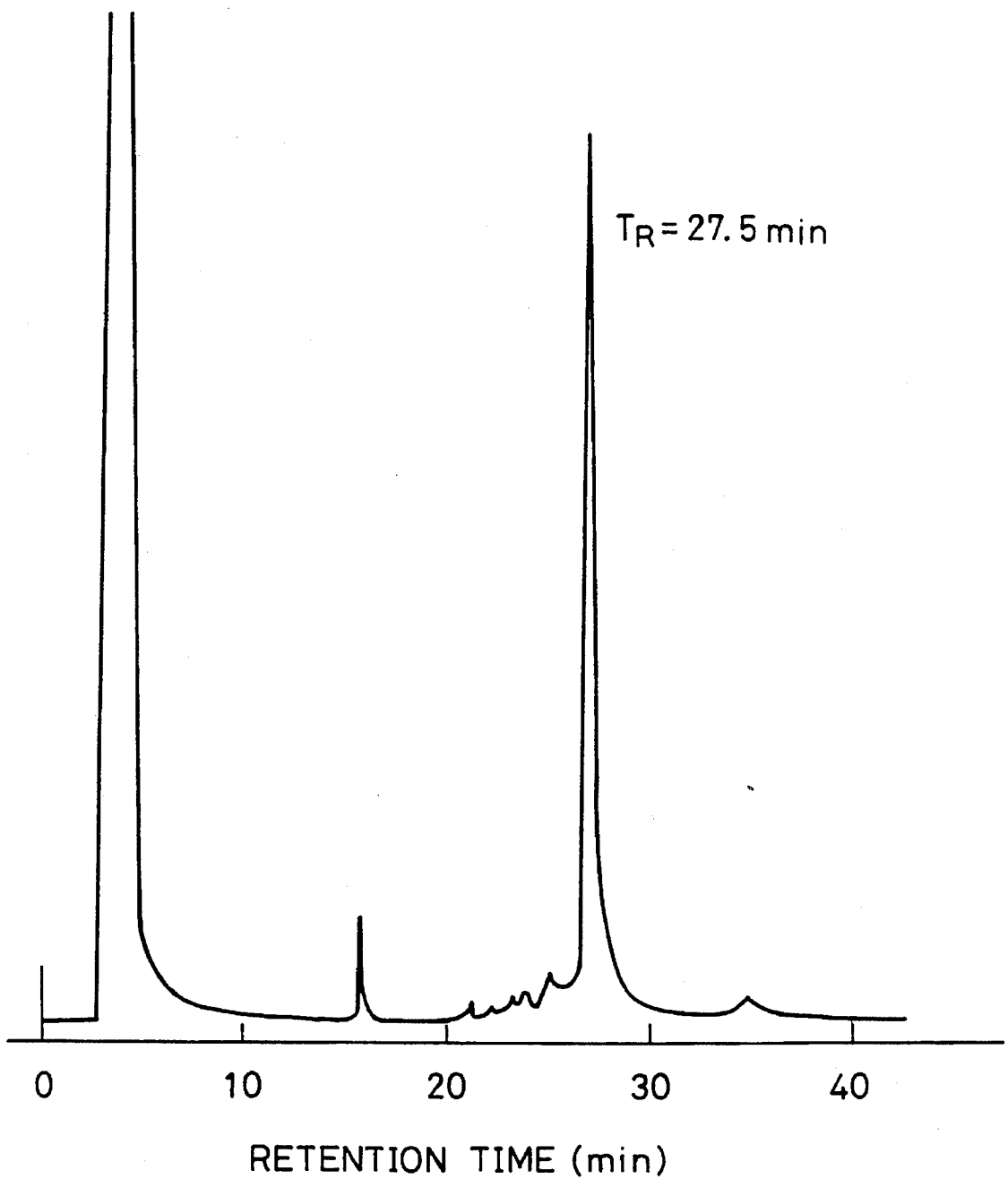
FIG. 1 is a chromatogram of the reversed phase HPLC analysis of a solubilized human BCDF in respect of which the disulfide linkage is in the reduced state.

The human BCDF was analyzed by a reversed phase HPLC column (214TP54 ex Vydac, 4.6 mm$\phi$×250 mm) as shown in FIG. 1. (The same conditions were employed hereinafter for the reversed HPLC). The analytical conditions are shown collectively in Table 1.

TABLE 1

HPLC Analytical Conditions

Column: Vydac "241TP54"
Eluent A: 0.1% TFA
Eluent B: 0.1% TFA and 80% acetonitrile
Elution program: 1 ml/min (linear gradient elution)

| Time (min) | A (%) | B (%) |
|---|---|---|
| 0 | 60 | 40 |
| 27 | 25 | 75 |
| 30 | 0 | 100 |

Detection: 280 nm (0.04 Abs)

Figure 2:
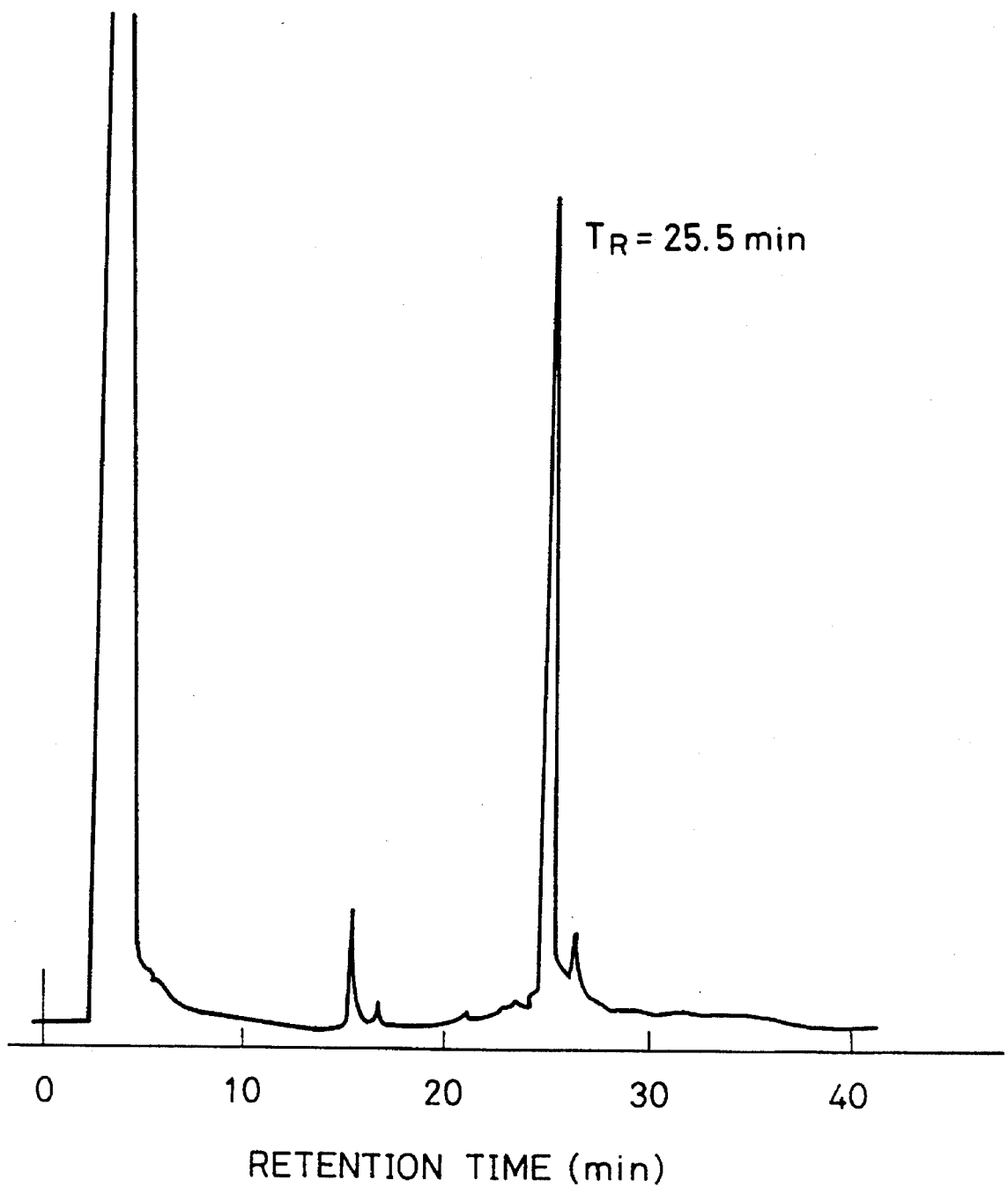
FIG. 2 is a chromatogram of the reversed phase HPLC analysis of a natural type human BCDF in respect of which the correct intramolecular disulfide linkage has been formed by refolding.

Subsequently, a 6M guanidine hydrochloride solution was added in such an amount that the human BCDF concentration became 0.7 mg/ml, and then the pH was adjusted to 8.5 by adding tris-hydrochloride in an amount of its final concentration of 10 mM and a small quantity of a sodium hydroxide solution. The resulting solution was stirred gently at room temperature for 15 hours to convert the human BCDF into one having intramolecular disulfide linkage. The peak of the human BCDF observed by the reversed phase HPLC analysis (the analytical conditions being the same as described above) was reduced in retention time by about 2 minutes as compared with that of the human BCDF immediately after extraction (FIG. 2).

A 2.4 liters portion of the obtained solution was fed to a "Sephadex G-25" column (25.2 cm$\phi$×25 cm, ex Pharmacia Inc.) equilibrated with a 10 mM sodium acetate buffer solution (pH 5.0), and developing was then conducted with the buffer solution to obtain 2.9 liters of a human BCDF fraction. The human BCDF purity was about 92%, and 88% of the protein used was recovered.

A "CM-Sepharose FF" column (11.3 cm$\phi$×9 cm, ex Pharmacia Inc.) equilibrated with the buffer solution was loaded with 4.5 liters of the human BCDF fraction obtained by repeating the procedure and then washed with 1 liter of the buffer solution. Eluting was carried out by using the buffer solution and a 0.5M sodium acetate buffer solution (pH 5.5). In this eluting operation, the ratio of the latter buffer solution was raised successively (linear gradient elution; flow rate =10 ml/min). The total amount of the eluent used was 10 times the column capacity. In this way, there was obtained a human BCDF fraction. The human BCDF purity was about 98% and 75% of the protein used was recovered. The endotoxin content was not more than 0.3 EU/mg human BCDF (as measured with an LAL assay kit "Toxicolor System" ex Seikagaku Kogyo KK).

A 100 ml (260 mg of human BCDF) portion of the obtained human BCDF fraction was diluted with 200 ml of distilled water to reduce the salt concentration to ⅓ of the initial value. Then, an aqueous 2N formic acid solution was added dropwise to adjust the pH of the human BCDF solution to 3.5. The resulting human BCDF solution was added with acetonitrile in such an amount that its final concentration became 10%, and stirred gently at room temperature for 5 minutes. A reversed phase HPLC column ("214TP1022" ex Vydac, 22 mm$\phi$×250 mm) equilibrated with a 0.5% sodium formate buffer solution (pH 4.0) was loaded with the human BCDF solution, and subjected to linear gradient elution (flow rate: 9 ml/min) with an eluting buffer solution (B) prepared by adding acetonitrile to the above-said buffer solution in an amount of a final acetonitrile concentration of 60%, whereby 63 ml of a human BCDF fraction (190 mg of human BCDF) was obtained. After the above purification treatment had been repeated, the human BCDF purity was higher than 99% (measured by the reversed phase HPLC, SDS-PAGE), the endotoxin content was not more than 0.01 EU/mg human BCDF, and 75% of the loaded human BCDF could be recovered.

Subsequently, the 63 ml human BCDF fraction obtained in the preceding step was loaded onto a "Sephadex G-25" column (9 cm$\phi$×5 cm, ex Pharmacia Inc.) equilibrated with a buffer solution of 20 mM acetic acid and 10% acetonitrile, followed by developing with the buffer solution to obtain a 150 ml human BCDF fraction. The column was this time equilibrated with a buffer solution (pH 4.5) of 5 mM sodium acetate, and loaded with a 75 ml portion of the fraction obtained in the preceding step. Developing was carried out with the buffer solution to obtain a 85 ml human BCDF fraction. As a result of this two-stage gel filtration process, 70% of the loaded human BCDF was recovered, and the acetonitrile in the solution was removed. The amount of the human BCDF aggregates formed in the process was about 5%.

Then, a "CM-Sepharose FF" column (5 cmϕ×2.5 cm, ex Pharmacia Inc.) equilibrated with a 20 mM sodium acetate buffer solution (pH 4.5) was loaded with 1.3 liters of the overall human BCDF fraction obtained in the previous step, and washed with 100 ml of the buffer solution. Eluting all at once with a buffer solution (pH 6.5) of 10 mM citric acid and 50 mM sodium chloride to obtain a 110 ml concentrated human BCDF fraction (750 mg of human BCDF). The amount of the human BCDF aggregates was not more than 5%, and 75% of the loaded human BCDF was recovered. The human BCDF concentration had risen to 6.8 mg/ml.

Figure 3:
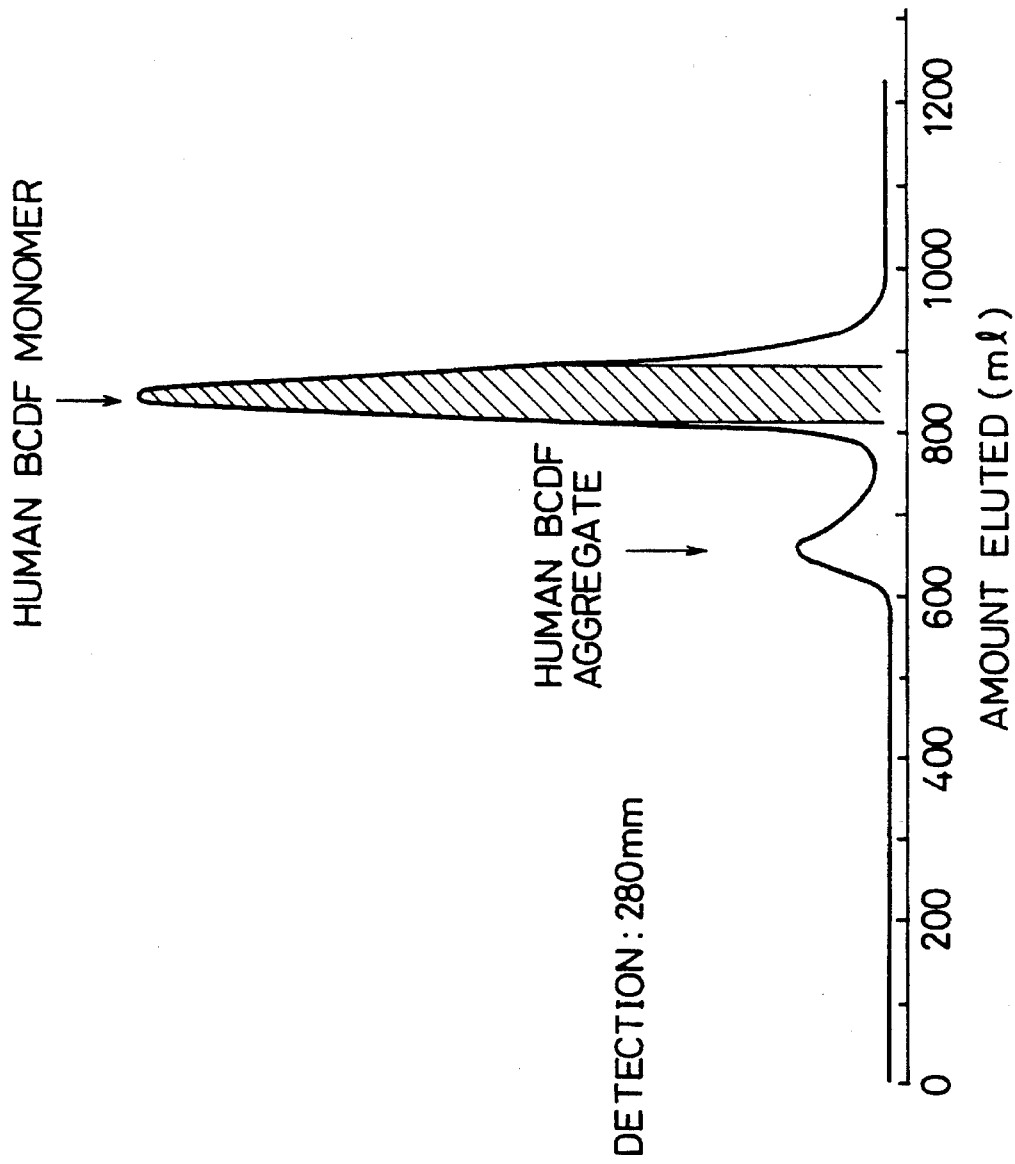
FIG. 3 is a chromatogram of a gel filtration chromatographic step for purifying a concentrated human BCDF solution.

Further, a 70 ml portion of the concentrated human BCDF solution obtained in the preceding step was loaded onto a "Superdex 75" preg grade column (6 cmϕ×60 cm, ex Pharmacia Inc.) equilibrated with a 10 mM sodium citrate buffer solution (pH 6.0), and developing was conducted with the buffer solution to obtain a 70 ml human BCDF monomer fraction (300 mg of purified human BCDF) (indicated by the hatched portion in FIG. 3).

Figure 4:
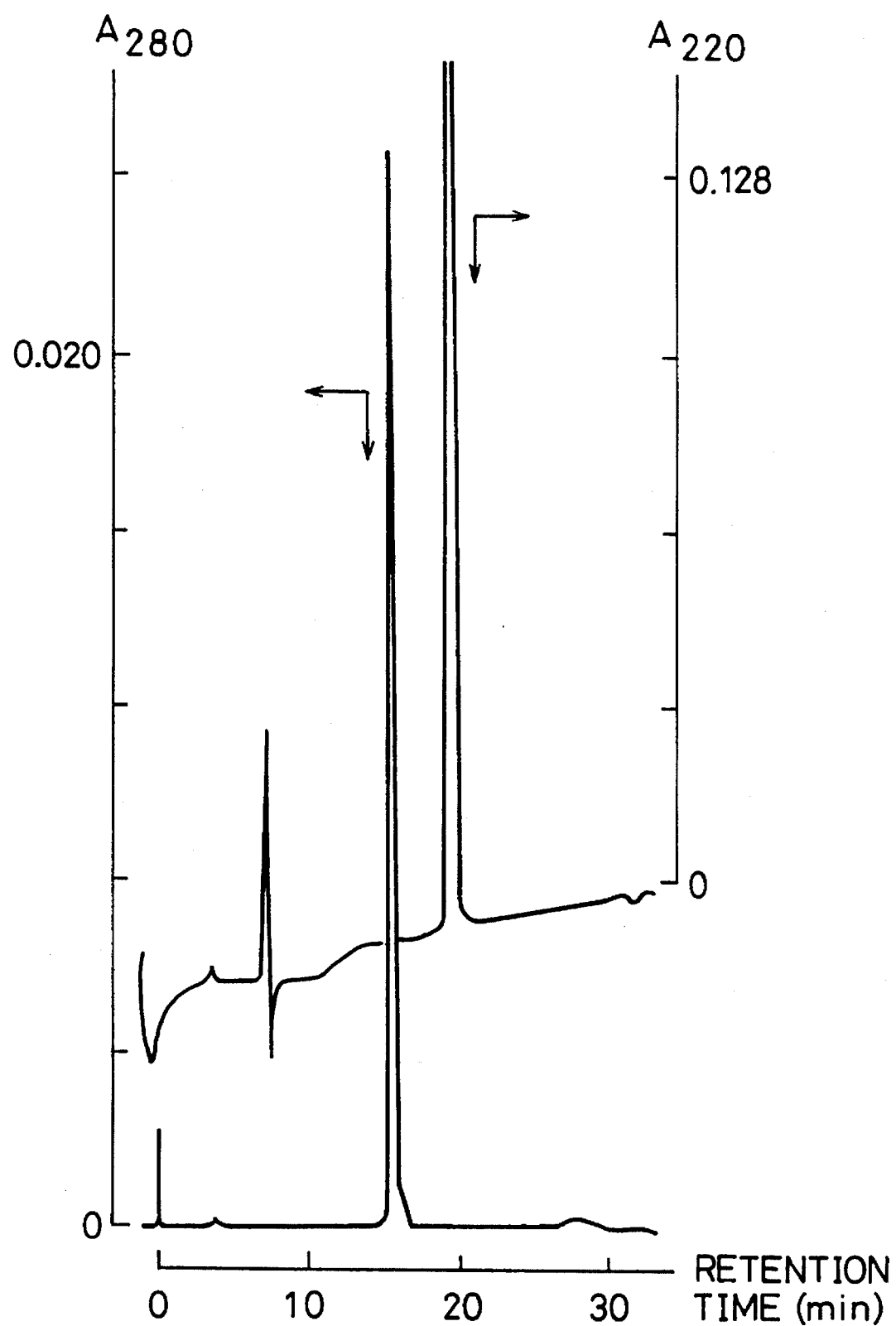
FIG. 4 is a reversed phase HPLC chromatogram of a purified human BCDF.

This purified human BCDF showed a single peak in each analysis by the reversed phase HPLC, the ion exchange HPLC and the gel filtration HPLC (see FIGS. 4, 5 and 6), and a single band by SDS-PAGE (silver dyeing). The conditions for these HPLC analyses are shown in Table 2 (a)–(c).

TABLE 2

| HPLC Analytical Conditions |

(a) Conditions for the reversed phase HPLC (human BCDF: 25 μg)
Column: "214TP54" (4.6 mmϕ × 250 mm, ex Vydac)
Eluent A: 0.05% tetrafluorobutyric acid
B: 0.05% tetrafluoroacetic acid and 80% acetonitrile
Elution program: 1 ml/min (linear gradient elution)

| Time (min) | A (%) | B (%) |
| --- | --- | --- |
| 0 | 50 | 50 |
| 20 | 25 | 75 |
| 22 | 0 | 100 |

(b) Conditions for the ion exchange HPLC
Column: "TSK SpNPR" (4.6 mmϕ × 3.5 mm, ex Tosoh)
Eluent A: 0.01M sodium acetate, pH 5.0
B: 0.5M sodium acetate, pH 5.5
Elution program: 1 ml/min (linear gradient elution)

| Time (min) | A (%) | B (%) |
| --- | --- | --- |
| 0 | 100 | 0 |
| 1.0 | 80 | 20 |
| 6.0 | 30 | 70 |
| 6.5 | 0 | 100 |
| 7.0 | 0 | 100 |

(c) Conditions for the gel filtration HPLC (purified human BCDF: 250 μg (100 μl))
Column: "Superdex 75HR" 10/30 (1 cmϕ × 30 cm, ex Pharmacia)
Eluent: 10 mM citric acid and 8.7 mM phosphoric acid; pH 7.0 (adjusted with a sodium hydroxide solution); flow rate: 0.8 ml/min In FIG. 5, the peak at about 0.5 minute is due to injection shock and that at about 6.37 minutes is attributable to the aggregates formed in the course of the analysis. Also, in FIG. 6, the peak at about 19 minutes is due to the salt in the sample.

By the Western blotting using a polyclonal anti-*Escherichia coli* antibody, there was detected no band attributable to contaminants. Also, the enzyme immunoassay using the antibody revealed that the inclusion of protein derived from *E. coli* was not more than several ppm, indicating that inclusion of such protein is of a very low level. The endotoxin content as determined by the LAL assay was not more than 0.01 EU/mg human BCDF. The overall recovery of human BCDF in the above-described purification process was 15%.

The purification process in the present example of this invention is outlined in Table 3.

TABLE 3

| Outline of Human BCDF Purification | | | | |
| --- | --- | --- | --- | --- |
| Purification steps | Reagents and conditions | Purification effect | Step yield | Total yield |
| Collection of insoluble granules | Fragmentation of bacterial cells; centrifugation | Removal of soluble bacterial cell components | — | — |
| Solubilization | 6 M guanidine hydrochloride; pH: about 5.5 | Perfect solubilization of human BCDF | 100% | 100% |
| Oxidation | 6 M guanidine hydrochloride; pH about 8.5; room temp.; 15 hr. | Formation of natural type disulfide linkage | 90% | 90% |
| Refolding | "Sephadex G-25"; 10 mM sodium acetate; pH 5.0 | Formation of natural type higher-order structure; removal of guanidine hydrochloride and insoluble bacetrial cell components | 88% | 79% |
| Cation exchange chromatography | "CM Sepharose FF"; sodium acetate; linear gradient; pH 5.0 → 5.5 | Removal of soluble bacterial cell components; removal of endotoxin | 75% | 59% |
| Reversed phase HPLC | "Vydac C₄" (300 Å); 0.5% sodium formate; pH 4.0; acetonitrile; | Removal of human BCDF analogs (primary structure variants); removal of endo- | 75% | 45% |

TABLE 3-continued

Outline of Human BCDF Purification

| Purification steps | Reagents and conditions | Purification effect | Step yield | Total yield |
|---|---|---|---|---|
| Removal of organic solvent | linear gradient "Sephadex G-25"; 20 mM acetic acid and 10% acetonitrile (1st stage); 5 mM sodium acetate (2nd stage) | toxin Removal of acetonitrile; prevention of formation of human BCDF aggregates (less than 5%) | 70% | 31% |
| Cation exchange chromatography | "CM Sepharose FF"; 20 mM sodium acetate → 10 mM sodium citrate and 50 mM NaCl; pH 6.5; stepwise gradient | Concentration of human BCDF; removal of product resultant from severance of peptide linkage | 75% | 23% |
| Gel filtration | "Superdex 75"; 10 mM sodium citrate; pH 6.0 | Removal of human BCDF aggregates | 65% | 15% |

EXAMPLE 2

With respect to a solubilized human BCDF solution (20 ml) obtained in the same way as in Example 1, there were carried out an oxidation reaction and a refolding treatment in the same way as in Example 1 except for what will be stated below. That is, the human BCDF concentration was fixed (0.7 mg/ml or 0.17 mg/ml) while the guanidine hydrochloride concentration was adjusted to 2–6M or 0.6M and the concentrations of the reduced type glutathione and the oxidized type glutathione were adjusted to 10–0 mM and 1–0 mM, respectively. Under these conditions, there was carried out the oxidation reaction, followed by a gel filtration chromatographic treatment. The gel filtration conditions were as shown in Table 4.

TABLE 4

Gel Filtration Conditions

Column: 2.6 cmϕ × 18 cm (96 ml)
Support: "Sephadex G-25" (ex Pharmacia Inc.)
Developing solution: 10 mM sodium acetate, pH 5.0
Detection: absorbance (280 nm)
Sample volume: 20 ml The results were as shown in Table 5.

TABLE 5

Gel Filtration Chromatographic Treatment

| Oxidation conditions | Recovery* | Disulfide linkage formed** |
|---|---|---|
| (1) 2M guanidine hydrochloride; pH 8.0; reduced type glutathione 10 mM, oxidized type glutathione 1 mM | 20% | Natural type |
| (2) 4M guanidine hydrochloride; pH 8.5; reduced type glutathione 10 mM, oxidized type glutathione 1 mM | 46% | Mixture of natural type and mixed disulfide linkages |
| (3) 6M guanidine hydrochloride; pH 8.5; reduced type glutathione 1 mM, oxidized type glutathione 0.1 mM | 90% | Mixture of natural type and mixed disulfide linkages |
| (4) 6M guanidine hydrochloride; pH 8.5; reduced type glutathione 0.01 mM, oxidized type glutathione 0.002 mM | 90% | Natural type |
| (5) 6M guanidine hydrochloride; pH 8.5; reduced type glutathione - not added oxidized type glutathione - not added | 90% | Mixture of natural type and intermolecular disulfide linkage (human BCDF dimer) |
| (6) 0.6M guanidine hydrochloride; pH 8.5; reduced type glutathione 1 mM, oxidized type glutathione 0.1 mM; human BCDF 0.17 mg/ml | 38% | Natural type. There existed 36% of reduced type in the solution and 22% of reduced type in the precititate. |

*Recovery is the rate of formation of natural type human BCDF after the passage of 15 hours from the start of the oxidation reaction, assuming that the amount of the reduced type human BCDF at the start of the oxidation reaction is 100%.
**Confirmation of the formed disulfide linkage was made by the reversed phase HPLC (the analytical conditions being the same as in the case of FIG. 1).
(Note) The human BCDF concentrations in the cases of the above-described oxidation conditions (1)–(5) were all 0.7 mg/ml.

Under the conditions of (3) in Table 5, the oxidation reaction proceeded rapidly (the reaction being completed in 3–6 hours) and the human BCDF recovery was also high, but disulfide mixed with glutathione was contained in the formed disulfide linkage. Under the conditions of (4) in the table, although the oxidation reaction proceeded slower (10–15 hours required for the reaction to be completed) than under the conditions of (3), the human BCDF recovery was high and the formed disulfide linkage was the natural type alone. Under the conditions of (5) in Table 5, although the human BCDF recovery was high, there was formed a human BCDF dimer in respect of which several % of the human BCDF had intermolecular disulfide linkage. As would be seen from (6) in the table, the human BCDF, unless the guanidine hydrochloride concentration is sufficiently high could not be recovered with high efficiency even if the human BCDF concentration is reduced to 0.17 mg/ml. This is attributable to re-precipitation of the starting solubilized human BCDF (reduced type human BCDF with substantially no disulfide linkage). Incidentally, the rate of loss in a precipitation fraction was further increased as the human BCDF concentration was increased.

It has thus been found that, with the use of a high-concentration guanidine hydrochloride and a low-concentration thiol disulfide reagent, the formation can be prevented of glutathione-mixed disulfide linkage or intermolecular disulfide linkage of human BCDF, whereby natural type human BCDF can be obtained in a high yield.

In this connection, confirmation of the formation of disulfide linkage was made by the reversed phase HPLC as shown in FIG. 1, confirmation of the formation of mixed disulfide linkage was made by detecting the increase in molecular weight measured by the mass spectrometry (MS), and confirmation of the human BCDF aggregates forming intermolecular disulfide linkage was made by the SDS-PAGE method (under the non-reducing condition).

EXAMPLE 3 by following the method disclosed in a prior literature (Uchida et al; Journal of Biomolecular NMR, 1, 49–64, 1991), two kinds of lavelled human BCDF were made by using as a nutrient an amino acid cysteine (Cys) and another amino acid phenylalanine (Phe), which is widely distributed as primary structure of human BCDF, respectively, their carbonyl carbons having been labelled with $^{13}C$, and were each purified by the method of Example 1.

In order to again refold the intramolecular disulfide linkage of human BCDF, 0.04 ml of 100 mM dithiothreitol (DTT) was added to 10 ml of an obtained human BCDF fraction, whereby the intramolecular disulfide linkage of human BCDF was reduced (confirmed by the reversed phase HPLC). The solution was then adjusted in pH to 5 with hydrochloric acid, and passed through a "Sephadex G-25" column equilibrated with 6M guanidine hydrochloride to perfectly remove the DTT. The obtained human BCDF fraction was diluted with 6M guanidine hydrochloride to decrease the human BCDF concentration to 0.7 mg/ml. Thereafter, there were again performed the oxidation reaction and refolding treatment under the conditions of (4) in Table 5 and the higher-order structure of the obtained human BCDF was observed by the $^{13}C$-NMR. The $^{13}C$-NMR spectrum of the backbone carbonyl carbons of protein can serve as a useful index for higher-order structure of protein molecules in a solution.

With respect to the two kinds of labelled human BCDF, there was no difference in $^{13}C$-NMR spectrum between that purified by the method of this invention and that purified according to the present invention and further subjected to re-refolding, and they each gave merely the signals corresponding to the respective amino acid residues (4 to Cys and 7 to Phe). It was, therefore, confirmed that a purified product according to this invention and an additionally refolded human BCDF are the same and uniform in higher-order structure.

The buffer solution for each of the two kinds of labelled human BCDF was substituted with a 0.1M borate buffer solution (pH 8.5). The human BCDF solution was added with DTT in an equivalent amount to one molecule of labelled human BCDF, and allowed to stand for 30 minutes. Then, its $^{13}C$-NMR spectrum was examined. It has been found that the presence or absence and the state of disulfide linkage can be inferred from the comparison between the $^{13}C$-NMR spectra of the oxidized type and the reduced type (including partially reduced type) of Cys-$^{13}C$ labelled human BCDF and the comparison between the spectra of human BCDF in respect of which $^{73}Cys$ and $^{83}Cys$ on the C terminal side are doubly labelled by $^{13}C$-$^{15}N$ double labelling from these, it has been found that a partially reduced type human BCDF in respect of which $^{73}Cys$ and $^{83}Cys$ are linked and $^{44}Cys$ and $^{50}Cys$ are in the non-linked state undergoes in a very short period of time intramolecular disulfide linkage (oxidation) at a pH of above 6.5, but at a pH of not more than 5, although the human BCDF exists relatively stable, intramolecular disulfide linkage takes place slowly.

Regarding oxidation and refolding of human BCDF, there are concerns about insufficient oxidation reaction or re-reduction. It has been found, however, that when the oxidation reaction and refolding treatment are conducted under the conditions of (4) in Table 5, there is formed no partially reduced type human BCDF.

EXAMPLE 4

From the human BCDF fraction (acetonitrile content: 45–55%) by the reversed phase HPLC obtained in Example 1, the organic solvent in the fraction was removed by the vacuum concentration method, the freeze-drying method and the gel filtration method under the conditions described below.

The results are shown in Table 6. The acetonitrile content in all the human BCDF fractions obtained by the gel filtration method was not more than 1%.

TABLE 6

| Removal of Organic Solvent | |
| --- | --- |
| Organic solvent removing conditions | Amount of human BCDF aggregates formed* |
| (1) Vacuum concentration | 60–80% |
| (2) Freeze-drying | 60–80% |
| (3) Gel filtration (one-stage treatment) 0.1% trifluoroacetic acid; pH 1.8 | 50–60% |
| (4) Gel filtration (one-stage treatment) 10 mM sodium acetate; pH 4.5 | 40–50% |
| (5) Gel filtration (one-stage treatment) 10 mM sodium citrate; pH 6.0 | 40–50% |
| (6) Gel filtration (one-stage treatment) 10 mM sodium phosphate, pH 8.0 | 40–50% |
| (7) Gel filtration (two-stage treatment) 20 mM acetic acid and 10% acetonitrile (1st stage); 5 mM sodium acetate, pH 4.5 (2nd stage) | <5% |

Figure 5:
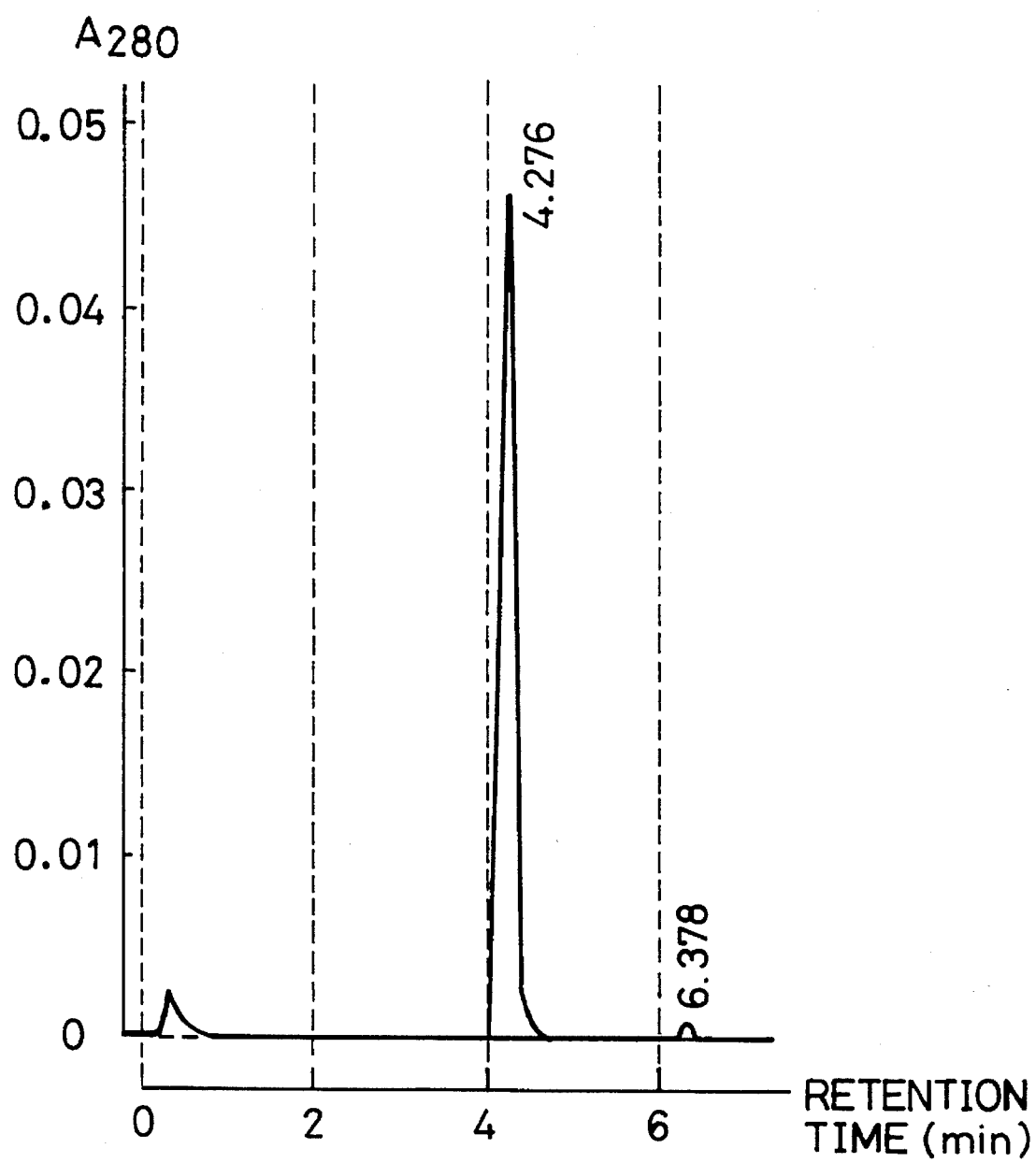
FIG. 5 is an ion exchange HPLC chromatogram of a purified human BCDF.
Figure 6:
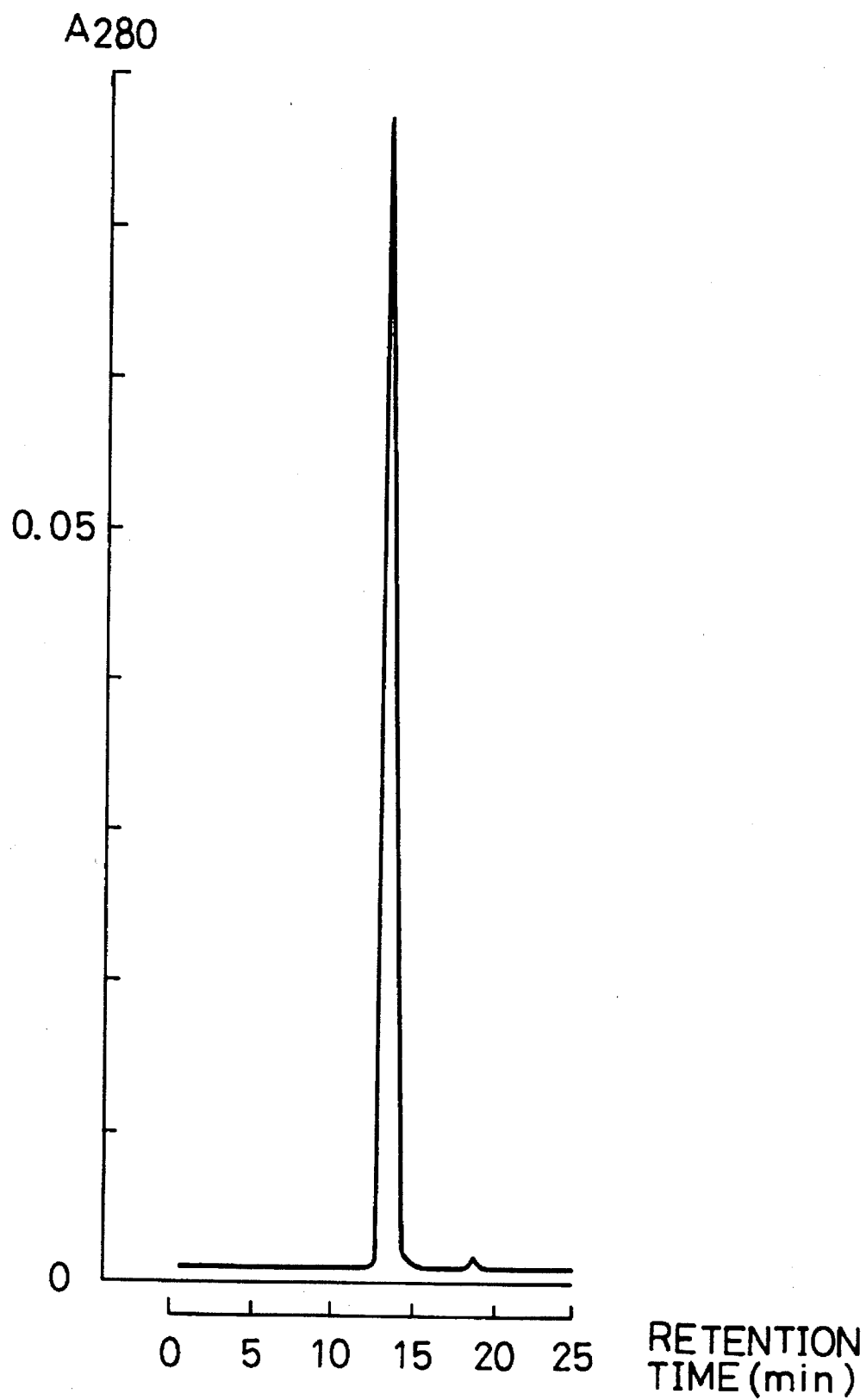
FIG. 6 is a gel filtration HPLC chromatogram of a purified human BCDF.

*the amount of the human BCDF aggregates formed was confirmed by the cation exchange HPLC (the analyzing conditions being the same as in the case of FIG. 5). It was confirmed by the GPC-LALLS method that the human BCDF aggregates are a dimer by non-covalent bonding of human BCDF.

The other conditions for removing the organic solvent that those described in Table 6 are shown in Table 7.

TABLE 7

| Organic Solvent Removing Conditions |
|---|
| (a) Vacuum concentration conditions ((1) in Table 6)<br>Apparatus: centrifugal evaporator "RD-31" (ex Yamato Science Co., Ltd.)<br>Degree of vacuum: 2 Torr<br>Heating: 40° C., 40 min.<br>Amount of sample: 5 ml |
| (b) Freeze-drying conditions ((2) in Table 6)<br>Apparatus: "Model TD-3" (ex FTS System Co., Ltd.)<br>Degree of vacuum: 10 mTorr<br>Heating: 5° C., 15 hr.<br>Amount of sample: 5 ml of sample was placed in a 10 ml vial. |
| (c) Gel filtration conditions ((3)–(7) in Table 6)<br>Column: 2.6 cm$\phi$ × 18 cm (96 ml)<br>Support: "Sephadex G-25" (ex Pharmacia)<br>Developing solution: shown in Table 6<br>Detection: absorbance (280 nm)<br>Sample: 14.4 ml ((3)–(6) and 1st stage of (7));<br>21.0 ml (2nd stage of (7)) |

From the above, it has been confirmed that the formation of human BCDF aggregates was unexpectedly suppressed by decreasing the organic solvent step-wise in the gel filtration method.

Industrial Applicability

According to the present invention, human BCDF produced by culturing a microorganism having a human BCDF gene integrated therein can be purified efficiently to a purity that enables us to use the BCDF for the therapeutical purposes. Further, the process of the present invention can be applied on an industrial scale, and, therefore, is a commercially utilizable one.

We claim:

1. A process for purification of human B-cell differentiation factor (BCDF) comprising solubilizing human BCDF in a human BCDF cultured broth obtained by culturing a microorganism having a human BCDF gene integrated therein;

contacting the solubilized human BCDF solution with 0.01 mM reduced glutathione and 0.002 mM oxidized glutathione;

adjusting guanidine hydrochloride concentration to 4–7M;

subjecting the resulting solution to gel filtration chromatography; and recovering said BCDF.

2. A process for separating a highly pure human BCDF from a human BCDF cultured broth obtained by culturing a microorganism having a human BCDF gene integrated therein, comprising the steps of:

(i) adjusting guanidine hydrochloride concentration to 4 to 7M, reduced glutathione concentration to 0.01 mM and oxidized glutathione concentration to 0.002 mM;

(ii) subjecting to an oxidation reaction a reduced type solubilized human BCDF solution formed by solubilizing human BCDF in a human BCDF cultured broth, and then subjecting to the gel filtration chromatography the resultant oxidized type human BCDF solution after adjusted to 4.0–7.0M in the guanidine hydrochloride concentration, (iii) conducting an ion exchange chromatographic treatment comprising feeding the human BCDF solution to a chromatographic column packed with a gel support having as ligand an ion exchanger whose base is a polysaccharide, dextran or a synthetic polymer, and then the elution being carried out with an eluent being changed in salt concentration, to thereby purify the human BCDF, (iv) conducting a reversed phase chromatographic treatment by passing the human BCDF solution through a column packed with a reversed phase chromatographic support having as ligand an alkyl group of 1–8 carbon atoms and with a pore size of 250 Å or more, to thereby purify the human BCDF, and (v) carrying out a gel filtration chromatographic treatment by first passing a developing solvent containing an organic solvent through a gel filtration chromatographic column, then feeding the human BCDF solution to the column with the amount of the organic solvent in the developing solvent being less than that in the first used developing solvent and decreased according to a stepwise gradient or linear gradient program, whereby an aqueous human BCDF solution cleared of the organic solvent is obtained.

3. A process for obtaining essentially pure human B-cell differentiation factor (BCDF) comprising the steps of:

solubilizing human BCDF in a human BCDF cultured broth to form a human BCDF solution;

adjusting guanidine hydrochloride concentration to 4 to 7M, reduced glutathione concentration to 0.01 mM and oxidized glutathione concentration to 0.002 mM;

subjecting said human BCDF solution to gel filtration chromatography; and recovering said BCDF.

4. The process according to claim 3, wherein said guanidine hydrochloride concentration is 5.0 to 6.0M.

5. The process according to claim 3, wherein the pH of said human BCDF solution is maintained at 6.5 to 9.0.

6. The process according to claim 5, wherein said pH is 8.0 to 8.6.

7. The process according to claim 3, wherein the temperature of said human BCDF solution is maintained at from 10° to 35° C.

8. The process according to claim 7, wherein said temperature is from 20°–28° C.

9. The process according to claim 3, wherein following said adjusting step, said human BCDF solution is stirred slowly for 3 to 24 hours.

10. The process according to claim 9, wherein said human BCDF solution is stirred for 10 to 15 hours.

11. The process according to claim 3, wherein following said gel filtration step said human BCDF solution is subjected to ion exchange chromatography.

12. The process according to claim 11, wherein said ion exchange chromatography step comprises contacting said human BCDF solution with chromatographic column packed with a gel support having as ligand an ion exchanger whose base is a polysaccharide, dextran or a synthetic polymer, and then eluting human BCDF with an eluent being changed in its salt concentration.

13. The process according to claim 12, wherein said eluent is acetic acid or formic acid.

14. The process according to claim 11, wherein following said ion exchange chromatography step and prior to said gel filtration step, human BCDF solution is subjected to reverse phase chromatography.

15. The process according to claim 14, wherein said reverse phase chromatography comprises passing said human BCDF solution through a column packed with a reversed phase chromatographic support having as ligand an alkyl group of 1–8 carbon atoms and with a pore size of 250 Å or more.

16. The process according to claim 14, wherein following said reversed phase chromatography, said human BCDF solution is subjected to a second gel filtration step.

17. The process according to claim 16, wherein said second gel filtration step comprises passing a first amount of a buffer solution comprising an organic acid and an organic solvent through a gel filtration chromatographic column, then loading said human BCDF solution onto said column, and then passing through said column a second amount of said buffer wherein the amount of organic solvent in said buffer is gradually decreased according to a stepwise gradient or linear gradient program.

18. A process for obtaining essentially pure human B-cell differentiation factor (BCDF) comprising the steps of:

solubilizing human BCDF to form a human BCDF solution;

adjusting the concentration of guanidine hydrochloride to 4 to 7M, the concentration of reduced glutathione 0.01 mM and the concentration of oxidized glutathione to 0.002 mM;

subjecting said human BCDF solution to gel filtration chromatography;

subjecting said human BCDF solution to reverse phase chromatography;

subjecting said human BCDF solution to gel filtration chromatography by passing a first amount of a buffer solution comprising an organic acid and an organic solvent through a gel filtration chromatographic column, then loading said human BCDF solution onto said column, and then passing through said column a second amount of said buffer wherein the amount of organic solvent in said buffer is gradually decreased according to a stepwise gradient or linear gradient program.

* * * * *